United States Patent [19]

Mauz et al.

[11] Patent Number: 4,767,620

[45] Date of Patent: Aug. 30, 1988

[54] CROSSLINKED POLYMERS WITH CARBONATE ESTER GROUPS, AND A PROCESS FOR THEIR PREPARATION

[75] Inventors: Otto Mauz, Liederbach; Siegfried Noetzel, Kelkheim; Klaus Sauber, Schwalbach am Taunus, all of Fed. Rep. of Germany

[73] Assignee: Hoechst Aktiengesellschaft, Fed. Rep. of Germany

[21] Appl. No.: 89,439

[22] Filed: Aug. 26, 1987

[30] Foreign Application Priority Data

Aug. 28, 1986 [DE] Fed. Rep. of Germany ....... 3629176

[51] Int. Cl.$^4$ .................... A61K 31/74; B32B 5/16; C08F 26/02; C08F 18/24
[52] U.S. Cl. ..................................... 424/78; 428/402; 526/302; 526/314; 526/212
[58] Field of Search ...................... 526/314, 302, 212; 428/402; 424/78

[56] References Cited

U.S. PATENT DOCUMENTS

| 2,384,115 | 9/1945 | Muskat et al. | 526/314 |
| 2,384,123 | 9/1945 | Muskat et al. | 526/314 |
| 4,098,771 | 7/1978 | Huemer et al. | 526/269 |
| 4,512,930 | 4/1985 | Romano | 526/314 |
| 4,542,069 | 9/1985 | Mauz et al. | 428/402 |
| 4,568,706 | 2/1986 | Noetzel et al. | 526/304 |

FOREIGN PATENT DOCUMENTS

491126 3/1953 Canada .................. 526/314

*Primary Examiner*—Joseph L. Schofer
*Assistant Examiner*—N. Sarofim
*Attorney, Agent, or Firm*—Finnegan, Henderson, Farabow, Garrett & Dunner

[57] ABSTRACT

Crosslinked polymers which are produced from monomers containing glycerol carbonate groups, crosslinking monomers and, where appropriate, other monoethylenically unsaturated monomers are composed of principally spherical porous particles and are very suitable as carrier materials for the immobilization of biologically active substances.

11 Claims, No Drawings

CROSSLINKED POLYMERS WITH CARBONATE ESTER GROUPS, AND A PROCESS FOR THEIR PREPARATION

The invention relates to crosslinked polymers which are predominantly in the form of spherical porous particles and whose structure is based on monomers containing glycerol carbonate groups, crosslinking monomers and, where appropriate, other monoethylenically unsaturated monomers. Polymers of this type are very suitable as carrier materials for the immobilization of biologically active substances.

The immobilization, via covalent bonds, of biologically active substances, such as, enzymes, antibodies, antigens, on hormones and the like, with retention of their activity, polymeric carrier materials, in order by this means, for example, to stabilize or purify enzymes or make them insoluble in water, is known. Biologically active substances immobilized in this manner offer considerable advantages compared with the soluble form: on the one hand, the removability, by sedimentation, after completion of a reaction is simplified and, on the other hand, the stability and reusability of the products are multiplied.

It is also known to use polymers and copolymers of vinylene carbonate for binding biologically active substances (see DE-A No. 2 407 340, DE-A No. 2 552 510). The cyclocarbonate groups still present after immobilization of the biologically active substances are converted into hydroxyl groups by a variant of the process described therein.

Although this known polymeric carrier material based on vinylene carbonate as reactive monomer unit has the advantage, compared with other carrier materials, that the non-specific adsorption of biologically active substances is less, it lacks the morphology of the bead form and the requisite porosity. Thus, for example, it cannot be used for column processes.

Irregularly shaped copolymers of vinylene carbonate are produced on polymerization in a non-polar organic dispersant in the presence of certain non-ionic dispersion stabilizers (see DE-A No. 25 56 759). These polymers are likewise not in the form of beads, nor do they have the necessary degree of porosity.

Furthermore, vinylene carbonate bead polymers which can be used for the preparation of carrier-bound biologically active substances are known (see DE-A No. 3 243 591). However, the preparation of these carrier copolymers must be carried out in hydrocarbons or liquid paraffin in the presence of certain dispersion stabilizers.

Modified polymers based on polyvinylene carbonate and/or polyhydroxymethylene are also known, the modification being effected by certain alkoxylated compounds incorporated in the polymer (see EP-A No. 161 464). It is necessary to use certain dispersion stabilizers in the preparation of these polymers, which are likewise suitable as carrier materials for biologically active substances or affinity chromatography. Once again, as a rule, the elaborate inverse suspension polymerization is necessary.

Thus the object was to find polymers for the immobilization of biologically active substances such as, for example, enzymes, which can be prepared in a very straight-forward manner and have a very good ability to bind biologically active compounds.

This has been achieved by use of porous, crosslinked polymers which contain glycerol carbonate ester groups and are in the form of beads or granules.

Thus the invention relates to a crosslinked polymer which is substantially composed of (A) 1 to 99% by weight of units derived from glycerol carbonate methacrylate, glycerol carbonate acrylate, glycerol carbonate vinyl ether and/or glycerol carbonate allyl ether, (B) 99 to 1% by weight of units derived from N,N'-divinylethyleneurea and/or N,N'-divinylpropyleneurea, with the total of the units always being 100% by weight, and with the polymer particles having substantially a spherical shape, a mean particle size of 10 to 600 $\mu$m and a mean pore diameter of 5 to 1,000 nm.

The invention also relates to a process for the preparation of the said polymer by copolymerization of the monomers in a liquid dispersant which, under the polymerization conditions, does not dissolve the monomers and the polymer, in the presence of a free radical initiator and other auxiliaries, and of a substance which dissolves readily in, or is miscible with, the monomers and is virtually insoluble in the dispersant (inert agent), which comprises copolymerization of (A') 1 to 99% by weight, based on the monomer mixture, of glycerol carbonate methacrylate, glycerol carbonate acrylate, glycerol carbonate vinyl ether and/or glycerol carbonate allyl ether and (B') 99 to 1% by weight, based on the monomer mixture, of N,N'-divinylethyleneurea and/or N,N'-divinylpropyleneurea, in the presence of 50 to 300% by weight, based on the total of the monomers, of inert agent.

Finally, the invention also relates to the use of the polymers thus obtained as carrier materials for the preparation of carrier-bound biologically active substances.

The polymer according to the invention is composed of (A) 1 to 99% by weight, preferably 3 to 60% by weight, in particular 8 to 50% by weight, of units derived from a monomer (A') containing glycerol carbonate groups, (B) 99 to 1% by weight, preferably 97 to 40% by weight, in particular 92 to 50% by weight, of units derived from a crosslinking monomer (B') and, where appropriate, (C) 0.1 to 10% by weight, preferably 0.1 to 5% by weight, of units derived from a monoethylenically unsaturated, non-hydrophilic and non-crosslinking monomer (C'). In each case the percentages by weight are based on the total polymer.

Examples of suitable monomers (A') containing glycerol carbonate groups are glycerol carbonate acrylate, glycerol carbonate vinyl ether and/or glycerol carbonate allyl ether, preferably glycerol carbonate methacrylate, alone or in a mixture. The monomers containing glycerol carbonate groups are prepared by, for example, the processes described in German Patent Applications Nos. P 35 29 263.6 and P 36 00 602.5 (filed on Aug. 16, 1985, and Jan. 11, 1986, respectively), by passing carbon dioxide into the corresponding monomers which contain epoxide groups and are dissolved in an organic solvent, in the presence of suitable catalysts, with the epoxide ring being converted into the carbonate ring by incorporation of the carbon dioxide molecule.

Examples of suitable crosslinking monomers (B') are N,N'-divinylpropyleneurea, but preferably N,N'-divinylethyleneurea, alone or in a mixture.

Suitable monoethylenically unsaturated, non hydrophilic and non-crosslinking monomers (C') are vinyl alkanoates, alkyl acrylates, alkyl methacrylates, styrene and styrene derivatives, preferably vinyl acetate, methyl methacrylate, butyl acrylate and styrene, alone or in a mixture.

In the process according to the invention for the preparation of the polymer according to the invention, the monomers are polymerized in the presence of a free radical initiator and further auxiliaries in a suspension, solution or precipitation polymerization process. Suspension polymerization in water as suspending agent and at a temperature of 20° to 120° C., preferably of 25° to 90° C., is preferred.

Suitable free radical initiators are those which are readily soluble in the monomer phase and sparingly soluble in water. Examples of these are organic peroxides such as di-tert.-butyl peroxide, dibenzoyl peroxide, bis(o-methylbenzoyl)peroxide, tert.-butyl hydroperoxide, cumene hydroperoxide, diisopropyl peroxydicarbonate and cyclohexanone peroxide, or aliphatic azo compounds such as $\alpha,\alpha'$-azodiisobutyronitrile, azobiscyanovaleric acid, 1,1'-azocyclohexane-1,1'-dicarbonitrile and azodicarbonamide.

Stabilizers and/or dispersing auxiliaries are used in the suspension polymerization, such as, for example, polyvinylpyrrolidone, polyacrylamide, polyvinyl alcohol or hydroxyethylcellulose.

In order to achieve as high a porosity of the bead polymer as is possible, certain inert, liquid components (inert agents) are added to the polymerization system or, preferably, to the monomers. These components are to be understood to be those materials in which the monomers are readily soluble or with which the monomers are miscible, but which, on the other hand, are virtually insoluble in the dispersant and thus are not miscible with it. According to their behavior toward the appropriate copolymers, the inert agents can be divided into swelling and/or precipitating agents. The inert agents do not take part in the polymerization, but are coated by the polymer and are dissolved out again during work-up. This produces permanent pores. The pore size can be affected by the type and amount of the inert agent, but also depends on the amount of crosslinking component.

The inert agents which are used in the polymerization and in which the monomers are dissolved must not in the present case react with the ethylenic double bonds and the glycerol carbonate groups of the monomers.

Preferred inert agents are pentanol, heptyl alcohol, 2-ethylhexanol, nonyl alcohol, decyl alcohol, lauryl alcohol, cyclohexanol and oxoalcohols, for example TCD alcohol M

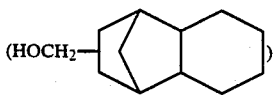

The inert agents are used in an amount of 50 to 300% by weight, preferably 100 to 250% by weight, in particular 125 to 200% by weight, based on the total amount of the monomers used. They can be used alone or in a mixture.

The process according to the invention is expediently carried out in a reaction vessel which is provided with a stirring device. The particle size of the bead polymer is adjusted in a known manner by the speed of stirring and the phase ratio. It is particularly advantageous to use a vertical cylindrical vessel which has a flat base and is provided with a stirrer which is located coaxially and whose shaft almost reaches the base of the vessel.

The reaction vessel is preferably vacuum-tight and can be provided with a reflux condenser, addition funnel, gas-introduction tube and temperature-measuring device. The heating and cooling of the vessel are generally brought about by a liquid bath, for example an oil bath or water bath.

It is advantageous to carry out the process according to the invention with the exclusion of atmospheric oxygen. Thus, before starting, the reaction vessel is flushed with an inert gas, preferably nitrogen.

After completion of the polymerization reaction, the unreacted monomers are removed from the reaction vessel, for example by evaporation under reduced pressure, preferably under a pressure of 0.1 to 15 torr. After removing the residual monomers, the dispersant is separated from the solid polymer, for example by decantation, filtration or aspiration of the supernatant. The polymer is then, where necessary, washed with a low-boiling organic solvent, for example a hydrocarbon, a lower alcohol or acetone, and finally dried. The polymer is usually dried at a temperature of 20° to 100° C., preferably of 40° to 80° C.; drying under reduced pressure is advisable in this process.

The bead polymer according to the invention is composed principally of spherical particles whose mean particle size in the dry, unswollen state is 10 to 600 $\mu$m, preferably 20 to 400 $\mu$m, and which preferably have a narrow particle size distribution. The particular optimum particle size of the polymer depends, in particular, on the specific area of use. For example, in a column process carried out under atmospheric pressure, it will be possible to select the particle size, within the limits mentioned above, to be correspondingly larger than for a process under elevated pressure. The beads of the bead polymer according to the invention are principally formed as macroporous beads. This is evident by the mean pore diameter which results according to the invention being in the range from 5 to 1,000 nm, preferably 10 to 800 nm.

The determination of the pore diameter (pore volume) is carried out in such a manner that first the pore volume is determined by the capillary pressure method (mercury porosimetry). In addition, a determination of the pore size is also possible by scanning electron microscopy.

The polymers according to the invention are suitable for the immobilization of biologically active substances by the formation of a covalent bond. However, they are also suitable, where appropriate after inactivation of the glycerol carbonate groups, for other purposes such as, for example, affinity chromatography etc.

The term "biologically active substances" is to be understood to be the known natural or synthetically prepared substances which are active in vivo or in vitro, for example enzymes, activators, inhibitors, antigens, antibodies, vitamins, hormones, effectors, antibiotics and proteins.

In this context, the term proteins also includes proteins having certain non-protein substituents, such as metal ions, polysacharides, porphyrin groups, adenine dinucleotide, ribonucleic acid, phospholipids etc. Polypeptide fragments, for example the active moieties of enzyme molecules, are also comprised by the term "biologically active substances".

Of the biologically active substances mentioned above, the enzymes are preferred. Examples of enzymes are urease, penicillin acylase, D-amino-acid oxidase, adenyl deaminase, alcohol dehydrogenase, asparaginase, carboxypeptidase, chymotrypsin, diphosphoesterase, α-glucosidase, glucose isomerase, glucose oxidase, glucose-6-phosphate dehydrogenase, hexokinase, invertase, β-lactamase, lactase, lactic dehydrogenase, various lectins, NAD kinase, neuraminidase, papain, peroxidase, phosphatases (alkaline and acid), 5'-phosphodiesterase, pyruvate kinase, ribonuclease and trypsin.

Examples of other biologically active substances are hormones, such as insulin and the wide variety of pituitary hormones, proteins of the gamma-globulin fraction, for example antihemophilic factor, the blood clotting factors, specific antibodies, for example hepatitis, poliomyelitis, measles, mumps, influenza or rabbit antibodies, antigens, such as hepatitis, polymomyelitis, measles, mumps, influenza or rabbit antigens for purification or stimulation of suitable antibody reactions, the antigen (after being made insoluble) remaining in the insoluble form and consequently being unable to penetrate into the body and harm it, as well as general body proteins, such as hemoglobin or albumin.

The binding of the biologically active substances to the polymeric carrier material is known per se and is generally carried out in such a way that the dry carrier material is added, for example, to an enzyme solution which is adjusted, using a buffer solution, for example 1.5 molar potassium phosphate solution in water, to a particular pH. After an immobilization time, which can be 1 to 72 hours, the carrier material is washed thoroughly at a particular temperature (for example 23° C.) with 1 molar sodium chloride solution and with the buffer solution. The specific activity on the moist carrier material is then determined, for example by automatic titration, after addition of the substrate which is to be cleaved.

The new polymers according to the invention have the following advantages: they can be prepared from low-cost commercially available starting materials; it is possible to use water as the suspending agent in the suspension polymerization; hydrocarbons and chlorinated hydrocarbons, which are necessary in inverse suspension polymerization are avoided.

The polymers in the form of beads have a very good ability to bind biologically active substances.

EXAMPLES (1) to (6) 200 ml of demineralized water, 3.2 g of disodium hydrogen phosphate and 2.0 g of polyvinylpyrrolidone of molecular weight 360,000 were initially introduced into a round-bottomed flask with a reflux condenser stirrer, thermometer and nitrogen introduction tube, and the mixture was then stirred at 25° C. for about 20 minutes until the polyvinylpyrrolidone had completely dissolved. Then, a solution composed of components (A'), (B') and, where appropriate (C') together with inert agent and 2 g of azoisobutyronitrile was added. The mixture was then slowly heated to a temperature of 65° C., while stirring and blanketing with nitrogen, and was maintained at this temperature, by means of a thermostatic oil bath, for 7 hours. After the mixture had been cooled to about 25° C., the resulting bead polymer was filtered off through a suction funnel, was stirred three times with one liter of water for 30 minutes each time and filtered off with suction, stirred four times with 1 liter of methanol for 30 minutes each time and filtered off with suction, and stirred twice with 1 liter of acetone for 30 minutes each time and filtered off with suction. The bead polymer moist with acetone was screened and dried in a drying oven at 50° C. under 0.267 bar of nitrogen overnight.

The yields, particle size distribution from the screening analysis and, where appropriate, the mean pore diameters and the pore volumes required for their determination are listed in Table 1.

(7) to (11) The solution of a biologically active substance in a buffer solution was added to 0.2 g of a carrier material prepared as in one of Examples 1 to 5. After immobilization at 23° C. for 72 hours (16 hours immobilization time for Example 10) the beads were thoroughly washed with 1 molar sodium chloride solution and with buffer solution. The yield of material moist from the suction filter, measured on a substrate using an automatic titrator, the corresponding dry weight, and the immobilization yield (=ratio of activity on carrier: activity made available) after balancing the initial activity and the activity in the wash water, and the $\eta$ value ($\eta$=activity found/activity made available less activity in the wash water) are listed in Table 2. The activity (U) is the conversion of 1 μmol of substance per minute, and the specific activity=

$$\frac{\text{conversion of 1 μmol of substance}}{\text{minutes} \times \text{gram}}$$

TABLE 1

|  |  | Examples | | | | | |
|---|---|---|---|---|---|---|---|
|  |  | 1 | 2 | 3 | 4 | 5 | 6 |
| Comp. A': | [g] | | | | | | |
| Glycerol carbonate methacrylate | | 50 | 20 | 40 | 40 | — | — |
| Glycerol carbonate allyl ether | | — | — | — | — | — | 20 |
| Glycerol carbonate vinyl ether | | — | — | — | — | 50 | — |
| Comp. B': | [g] | | | | | | |
| N,N'—Divinyl-ethylene-urea | | 50 | 80 | 50 | 50 | 50 | 80 |
| Comp. C': | [g] | | | | | | |
| Vinyl acetate | | — | — | — | 10 | — | — |
| Methyl acrylate | | — | 10 | — | — | — | — |
| Inert agent: | [g] | | | | | | |
| Cyclhexanol | | 108 | 108 | 108 | 108 | 108 | 108 |
| Lauryl alcohol | | 12 | 12 | 12 | 12 | 12 | 12 |
| Yield | [g = % d.Th.] | 75 | 86 | 90 | 90.6 | 84.5 | 92.0 |
| Particle: size | [%] | | | | | | |
| >300 μm | | — | — | — | — | — | — |
| 200–300 μm | | — | — | 3.3 | — | — | — |
| 100–200 μm | | 36.0 | 53.0 | 26.9 | 35.4 | 53.4 | 51.7 |
| 50–100 μm | | 60.2 | 46.3 | 68.1 | 60.0 | 42.8 | 43.8 |
| <50 μm | | 3.8 | 0.7 | 1.7 | 4.5 | 3.8 | 4.5 |
| Spec. pore volume | [cm³/g] | 0.92 | — | — | 0.68 | — | 0.74 |
| Pore diameter | [nm] | 60 | — | — | 75 | — | 54 |

TABLE 2

|  | Examples | | | | |
|---|---|---|---|---|---|
|  | 7 | 8 | 9 | 10 | 11 |
| Carrier material of example | 1 | 2 | 3 | 4 | 5 |
| Biol. active substance (solution) \|μl\| | | | | | |
| Penicillin acylase | 1200 | 1200 | — | — | — |
| Trypsin | — | — | 1000 | — | — |
| Urease | — | — | — | 1000 | — |

TABLE 2-continued

| | Examples | | | | |
|---|---|---|---|---|---|
| | 7 | 8 | 9 | 10 | 11 |
| Chymotrypsin | —, | — | — | — | 700 |
| containing [μg/ml] | 30 | 30 | 6.25 | 30 | 6 |
| corr. to [U/ml] | 220 | 240 | 475 | 45 | 1001 |
| Buffer solution [molar] | | | | | |
| Potassium phosphate | 1.5 | 1.5 | 1.0 | 1.0 | 1.0 |
| Benzamidine | — | — | $1,6 \times 10^{-2}$ | — | — |
| pH | 7.6 | 7.6 | 7.8 | 8.0 | 8.0 |
| Titration conditions: | | | | | |
| Temp. [°C.] | 37 | 37 | 37 | 30 | 37 |
| pH- | 7.8 | 7.8 | 8.1 | 6.1 | 8.9 |
| Substrate | A | A | B | C | D |
| Yield [mg] | 456 | 544 | 495 | 497 | 566 |
| (moist from suction funnel) | | | | | |
| Corr. 2 [U/g] | 296 | 288 | 356 | 55 | 510 |
| Based on [U/g] | 675 | 785 | 880 | 137 | 1445 |
| dry weight | | | | | |
| Immobilization [%] | 51 | 60 | 37 | 60 | 41 |
| yield | | | | | |
| η- Value | 0.57 | 0.61 | 0.38 | 0.65 | 0.41 |

Substrate:
A = potassium penicillate
B = N'—benzoyl-L-arginine ethyl ester hydrochloride (BAEE)
C = urea
D = acetyltyrosine ethyl ester

We claim:

1. A crosslinked polymer substantially composed of (A) 1 to 99% by weight of units derived from at least one component selected from the group consisting of glycerol carbonate methacrylate, glycerol carbonate acrylate, glycerol carbonate vinyl ether and glycerol carbonate allyl ether, (B) 99 to 1% by weight of units derived from N,N'-divinylethyleneurea, N,N'-divinylpropyleneurea or both, with the total of the units always being 100% by weight, and with the polymer particles having substantially a spherical shape, a mean particle size of 10 to 600 μm and a mean pore diameter of 5 to 1,000 nm.

2. A polymer as claimed in claim 1, wherein glycerol carbonate methacrylate is used.

3. A polymer as claimed in claim 1, which additionally contains (C) 0.1 to 10% by weight, based on the total polymer, of units which are derived from at least one component selected of the group consisting of vinyl acetate, methyl methacrylate, butyl acrylate and styrene.

4. A process for the preparation of a crosslinked polymer which comprises copolymerization of (A') 1 to 99% by weight of at least one component selected of the group consisting of glycerol carbonate methacrylate, glycerol carbonate acrylate, glycerol carbonate vinyl ether and glycerol carbonate allyl ether and (B') 99 to 1% by weight of N,N'-divinylethyleneurea, N,N'-divinylpropyleneurea or both, the total of the monomers always being 100% by weight in a liquid dispersant which, under the polymerization conditions, does not dissolve the monomers and the polymer (suspending agent), in the presence of a free radical initiator and other auxiliaries and of 50 to 300% by weight, based on the total of the monomers, of an inert agent.

5. The process as claimed in claim 4, wherein additionally the component (C') 0.1 to 10% by weight, based on the monomer mixture, of at least one component selected of the group consisting of vinyl acetate, methyl methacrylate, butyl acrylate and styrene is copolymerized.

6. The process as claimed in claim 4 wherein principally spherical particles with a mean particle size of 10 to 600 μm and a mean pore diameter of 5 to 1,000 nm are prepared.

7. The process as claimed in claim 4 wherein the copolymerization is carried out as suspension polymerization in water as suspending agent at a temperature of 20° to 120° C.

8. The process as claimed in claim 4, wherein the inert agent is pentanol, heptyl alcohol, 2-ethylhexanol, nonyl alcohol, decyl alcohol, lauryl alcohol, cyclohexanol or an oxoalcohol.

9. The process as claimed in claim 8 wherein the oxoalcohol is TCD alcohol M

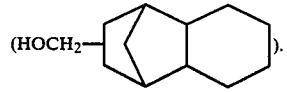

10. Immobilized biologically active substance prepared with the polymer as claimed in claim 1 as carrier material.

11. Immobilized biologically active substance as claimed in claim 10, wherein the biologically active substance is an enzyme.

* * * * *